United States Patent [19]

Meyer

[11] Patent Number: 5,322,697

[45] Date of Patent: Jun. 21, 1994

[54] COMPOSITION AND METHOD FOR INDUCING SATIETY

[76] Inventor: James H. Meyer, 2210 La Mesa Dr., Santa Monica, Calif. 90402

[21] Appl. No.: 889,710

[22] Filed: May 28, 1992

[51] Int. Cl.$^5$ .................. A61K 9/54; A61K 9/62; A61K 31/195; A61K 37/00

[52] U.S. Cl. .................. 424/458; 424/451; 424/457; 424/461; 424/489; 424/490; 424/494; 514/909; 514/910

[58] Field of Search ............ 424/451, 457, 458, 489, 424/490, 461, 494; 514/909, 910, 911

[56] References Cited

U.S. PATENT DOCUMENTS

| | | | |
|---|---|---|---|
| 4,491,578 | 1/1985 | Peikin | 514/2 |
| 4,623,539 | 11/1986 | Tunc | 424/78.17 |

Primary Examiner—Thurman K. Page
Assistant Examiner—James M. Spear
Attorney, Agent, or Firm—Robert J. Koch; Peter J. Davis

[57] ABSTRACT

A composition and method for the control of appetite having food grade nutrients as the active ingredients, and a pharmaceutically acceptable delivery agent, formulated so that the active ingredient is released predominantly in the ileum. The active ingredient may include sugars, fatty acids, polypeptides, and amino acids. The delivery agent may be a pH sensitive coating, a cellulosic polymer coating or a diazotized polymer. The composition may be formulated into pellets of between 1 and 3 mm with a density of around 1.0. The composition may be administered with a liquid as a slurry, or it may be administered in a tablet form. The composition may be used in conjunction with any weight loss or weight maintenance program.

10 Claims, 3 Drawing Sheets

COMPOSITION AND METHOD FOR INDUCING SATIETY

BACKGROUND OF THE INVENTION

1. Field of the Invention

This invention relates to a composition and method for controlling appetite in humans. More particularly, the invention concerns the targeting of nutrients for the ileum to induce satiety in a human being.

2. Related Technology

A major class of weight control agents are drugs which act on the central nervous system (CNS) to suppress appetite. One major subclass of CNS appetite suppressant drugs interacts with cathecolaminergic receptors in the brainstem. These include controlled drugs such as amphetamine, phenmetrazine, and diethylproprion, and over-the-counter drugs such as phenylpropanolamine. Manizidol is another CNS active drug which, although not a catecholamine, activates the central nervous system. Each of these agents have potential for addiction and, at doses which effectively reduce appetite, i.e., suppress food intake by 20-30%, they induce significant CNS side effects, such as nervousness, loss of concentration, and insomnia. Another subclass of CNS active appetite control drugs interferes with serotonergic systems. D-fenfluramine, for example, releases and depletes brain serotonin, but it causes sedation at appetite suppressant levels, and it may precipitate depression upon its withdrawal. Fluoxetine is an inhibitor of serotonin re-uptake in the brainstem. However, at effective appetite control doses, Fluoxetine often causes nausea and asthenia, i.e., weakness, lassitude.

Another major class of weight control agents are drugs which promote malabsorption of nutrients through suppression of digestive enzymes. One agent in this category is Acarbose, a bacterial inhibitor of amylase and brushborder glycosidases. Another is tetrahydrolipostatin, a fungal inhibitor of lipases. These agents work by preventing digestion of carbohydrates and/or fats, thus creating an effective reduction in the number of calories absorbed, despite continued consumption. One drawback is that virtually complete inhibition of the respective enzymes must be maintained throughout the digestive period, a situation that can be rarely achieved. Thus, Acarbose was shown to be ineffective in humans, and tetrahydrolipostatin was shown to reduce human absorption of fat by only 30%. A second major drawback to this approach is that subjects taking these agents develop hyperphagia for other foodstuffs. For example, subjects taking tetrahydrolipostatin will consume more carbohydrate to compensate for the loss of fat absorption. Thus, the loss of calories from malabsorption is compensated by an increased intake of food, especially of foodstuffs of a different class.

A third class of weight control agents are noncaloric, non-nutritive dietary substitutes, like saccharin or Nutrasweet, sugar substitutes, and sucrose polyester, a fat substitute. These agents, while not absorbed, provide a taste and/or texture like the nutrient for which they are substituted. The disadvantage of these substitutes is that persons develop a hyperphagia to compensate for the reduction of calories by the substitution. With sucrose polyester, a nondigestible lipid, fat soluble, enterohepatically circulated vitamins partition into the unabsorbed polyester and are lost from the body, a potential problem which can also occur with tetrahydrolipostatin.

Thermogenic drugs are also sometimes used. The catecholamine drugs discussed above have some thermogenic activity, in addition to their suppression of appetite. Thyroid hormone is also commonly used.

Semi-starvation diets are universally effective in short term weight loss, but regain of weight after resumption of less restricted diets is the rule. Long term use of semi starvation diets is nutritionally unsound because of the development of multiple deficiencies of essential nutrients.

Surgical devices have also been employed to control appetite. Intragastric balloons have been placed endoscopically according to the theory that they increase the amount of gastric distension and thus augment satiety responses. However, they have been discontinued because, while they were not shown to be any better than restricted diets in promoting weight loss, their long term use was associated with severe side effects such as gastric ulceration and migration of the balloons into the small intestine resulting in intestinal obstructions.

Patients with morbid obesity (body mass index $>29$ kg/m2, about 3% of the overweight population) are often encouraged to undergo bariatic surgery because, as a class, they suffer from more than four times the incidence of diabetes, cardiovascular disease, uterine and breast cancer, degenerative joint disease, and social stigmatization. Ileojejunal bypass, the first such surgery undertaken 30 years ago, has now been abandoned because of severe side effects such as poor subsequent malnutrition, fatal cirrhosis or renal failure. Biliopancreatic by-pass, gastric by-pass, and gastric partitioning (stapling) are the current procedures, but the long term side effects have not yet been determined.

BRIEF DESCRIPTION OF THE INVENTION

It is an object of the present invention to provide a composition and method for controlling appetite in animals that avoids the disadvantages and side-effects associated with the known compounds, compositions, and methods.

Accordingly, there is provided a composition comprising: a pharmaceutically acceptable satiety agent which may include at least one active ingredient selected from the group consisting of food grade nutrients (natural foodstuffs), and a pharmaceutically acceptable delivery agent, formulated for predominant release of the active ingredients in the ileum. Food grade nutrients may include but are not limited to sugars, free fatty acids, polypeptides, amino acids and suitable foods that are precursors thereto. According to one embodiment of the invention, the active ingredient is selected from the group consisting of sugars, free fatty acids, phenylalanine polypeptides, and amino acids. According to another embodiment, the active ingredient may include monomeric sugars, such as glucose and xylose. Furthermore, chemical derivatives or chemical analogs of "sensed" natural foodstuffs may be used in place of, or together with, natural foodstuffs to enhance the potency of the satiety response, through more favorable solubility, buffered ph, absorption, affinity to nutrient sensors in the intestine, or some combination of these properties. For example, dodecylsulfate is an analog of decanoate, a natural foodstuff. Sodium dodecanoate and sodium dodecylsulfate are preferred active ingredients. Pharmaceutically acceptable delivery agents include ion exchange resins and enteric coatings, such as pH sensitive polymers, diazotized polymers, and cellulosic polymers. There is further provided a method for controlling appetite comprising a) selecting an active ingredient from the group consisting food grade nutrients, b) selecting an enteric coating from the group consisting of pH sensitive polymers, diazotized polymers, and cellulosic polymers, c) encapsulating the selected active ingredient with the selected enteric coating into particles of between 1 and 3 millimeters in diameter with a density of between 0.5 and 2.0, and d) orally administering an effective dosage to an animal. The method further comprises releasing the active ingredient predominantly in the ileum. Once release begins, it occurs over the length of the ileum.

The present invention is a synthesis of several discoveries which have been pioneered by the inventor.

The intestines are responsible for a portion of satiety feedback. However, the inventor has found that the small intestine is much more sensitive to nutrient stimulus in triggering satiety than is the large intestine. In addition, it was discovered that the intensity of a satiety response to nutrients in the intestines is proportional to the length of bowel over which the nutrients are absorbed. Finally, the inventor demonstrated for the first time that artificially retarding the rate of absorption of a nutrient in the ileum, which under natural conditions is immediately and entirely absorbed as soon as it enters the ileum, magnifies the potency of the nutrient in eliciting an ileum initiated satiety response. The term "artificially" as used in the context of this invention means actively and purposefully influenced by, or controlled by, man.

Thus, the present invention is a novel and unobvious integration of the aforementioned discoveries of powerful satiety responses to nutrients in the ileum, the summation of sensory response with length of bowel contacted by the nutrient stimulus and, in turn, the enhancement of nutrient potency by artificially retarding its rate of absorption and thus extending its length of intestinal contact to trigger more sensors. Accordingly, a preferred embodiment of the present invention takes advantage of all three of these discoveries through the slow release from enteric coated, multiparticulate dosage forms which release small amounts of nutrients at different dissolution times to create a spread of nutrients and achieve the highest release and absorption profiles in ileum, the site of the most effective satiety sensation. A release profile simply reflects the amount of nutrient released by a delivery agent at any point along the digestive tract. An absorption profile of a specific nutrient reflects the absorption of that nutrient at any point along the digestive tract.

The enteric coated nutrient may be administered as tablets or as a slurry drink, with or between meals. The dosage form may be designed to promote ileal release and spread at the time of the next scheduled feeding. In this fashion, a very small amount of nutrient, less than 5 g for example, may produce a marked satiety effect.

The appetite control composition of the invention may be used as an adjunct to a weight loss program to reduce increased hunger or craving for food during the forced restriction in caloric intake. Alternatively, the composition of the invention may be used as a direct weight-loss-maintenance device, effective by virtue of the ability of the composition to reduce food intake by about 40%; or as an adjunct to a restricted weight-loss-maintenance diet, effective by virtue of the ability of the composition to induce satiety.

DETAILED DESCRIPTION OF THE INVENTION

One of the primary feedback mechanisms influencing appetite and satiety is the presence of nutrients in the gastrointestinal tract. Although gastric distension, i.e., stomach stretch, is considered by most researchers to be the single most important satiety signal, some researchers have suggested that the presence of nutrients in the intestines may contribute to satiety feedback. However, the preconception is so strong that gastric distension is paramount, that most researchers argue that intestinal nutrients act only through the slowing of gastric emptying of food, thereby indirectly promoting gastric distension, and thus, even more indirectly, contributing to satiety.

This invention is based in part on the inventor's discovery that the absorption of nutrients from the intestines triggers a powerful satiety feedback, independent of gastric distension.

Additionally, the inventor has also found that the distal intestine is more sensitive to nutrients than the proximal intestine, such that the same amount of nutrient will produce more satiety in the ileum than it would have in the jejunum. Again, this effect was discovered to occur independently of gastric or intestinal stretch.

Some of these studies were made in dogs with biliary fistulas. It was discovered that food intake in these dogs was significantly reduced when bile was diverted from the jejunum so as to increase the amount of unabsorbed, but digested fat reaching the ileum. The idea that satiety was more potently stimulated from ileum than from jejunum was further supported by studies in other dogs equipped with chronically implanted perfusion catheters to allow perfusion selectively of jejunum and of ileum. In these dogs, a fat-containing solution of sugar and peptides inhibited food intake significantly more potently when perfused into ileum than when perfused into jejunum. In most recent studies in still other dogs with pancreatic fistulas, diverting endogenous pancreatic enzymes from their normal entry into duodenum to enter, instead, at mid intestine reduced food intake in eleven flee-feeding dogs over eight day feeding periods reproducibly to as low as 70% of control. Displacing the digestion of food from proximal to distal bowel, when digestive enzymes were diverted there, exposed ileal sensors to much higher concentrations of nutrients than normal, resulting in an augmented satiety response. In these experiments, ileal volume flows were not increased. Yet these dogs had normal to slow rates of gastrointestinal transit so that this result was not a matter of gastric or ileal distension or aversive conditioning.

The invention also encompasses the discovery that the intensity of a biological response to the presence of nutrients in the small intestine is dependent upon the intensity of the stimulus per unit length of bowel and the length of bowel contacted. Specifically, it was observed that the magnitude of pancreatic secretion and gastric emptying responses to nutrients in the ileum varied in proportion to the length of bowel contacted by the nutrient. At maximum nutrient concentrations, the response became simply proportional to the length of bowel contacted by the stimulus.

For example, hydrogen ions, which are known to stimulate pancreatic secretion, were found to be potent even at a low initial concentration if they are bound (i.e., prevented from release and absorption) to weak acid anions that carry them downstream or are slowed from diffusion out of the bowel lumen by increased luminal viscosity and/or by encapsulation within the interstices of liver particles.

In another study, the inventor found that infusing 1.1 mmoles/min of glucose into the duodenum of dogs produced about half as much inhibition of gastric emptying as infusing 0.25 mmoles/min simultaneously into the 1st, 2nd, 3rd, and 4th quarters of the small intestine. This study demonstrated that the spread of glucose over the small intestine would augment its stimulated response, i.e., inhibition of gastric emptying.

The inventor hypothesized that if absorption of particular satiety inducing nutrients could be reduced or delayed, and length of small intestinal mucosal contact increased, the satiety response could be significantly magnified.

Normally, however, nutrients are rapidly absorbed and quickly disappear from the intestinal lumen because of active transport carriers or facilitated diffusion. The inventor has discovered, however, that increasing luminal viscosity and delaying availability, by the encapsulation of satiety inducing nutrients within enteric coated multi-particulates, the nutrients could be selectively delivered to and spread out over the more sensitive ileum.

By entericly coating nutrients in small spheres of different sizes (i.e., "multi particle dosage forms"), the satiety inducing nutrients may be delivered to and spread out over the ileum. First, the transit of spheres from stomach to intestine and along small intestine varies with sphere size and density. Therefore, the individual spheres spread out along small intestine as they move into and through it. Second, the rate of dissolution of the enteric coating varies to some degree from sphere to sphere. This variation further increases the length of small intestine over which the nutrient is released. Normally, nutrients would be absorbed rapidly once they enter small intestine, so that they usually are almost entirely absorbed before mid intestine. Since the enteric coatings on the spheres prevent the release of the nutrients until the coating dissolves, the distance over which a small amount of nutrient can be spread without being absorbed depends on (a) the transit characteristics of the spheres and (b) the rate of dissolution of the coating. Thus, a multi-particle dosage form is a means of achieving a long spread of contact between nutrient and intestinal mucosa. Furthermore, if release is programmed to occur in distal small intestine (ileum), higher luminal viscosity there will also serve to retard absorption and to further spread the released nutrient.

Since satiety feedback from distal small bowel (ileum) is more intense per amount of sensed nutrient than from proximal bowel (jejunum), timing the release (i.e., time to coating dissolution) to predominate in ileum will also enhance the satiety response per amount of agent ingested. Thus, both the spread and predominant site of delivery (ileum) will maximize the effect, so that a small amount of released nutrient will be sensed as though it were a large amount, creating a high satiating effect.

Finally, if the agent is also ingested so that its release in the ileum coincides with the time of the next scheduled feeding, the useful satiety response will be maximized. The time of emptying from the stomach is generally 2 hours. The time of intestinal transit is 2–4 hours. Thus, if the dosage form is taken with a meal, a medium time of gastric emptying of 2 hours, followed by dissolution of the enteric coating after reaching ileum in another 2–4 hours will maximally enhance satiety 4–6 hours later, at the time of the next meal.

This system is designed to maximize satiety feedback from normal intestinal sensors by small amounts of nutrients or nutrient derivatives, in essence, to "fool" body sensors which are not usually in contact with nutrients unless very large amounts are ingested. One significant advantage of this approach is one of minimal or no toxicity.

Study 1

Figure 1:
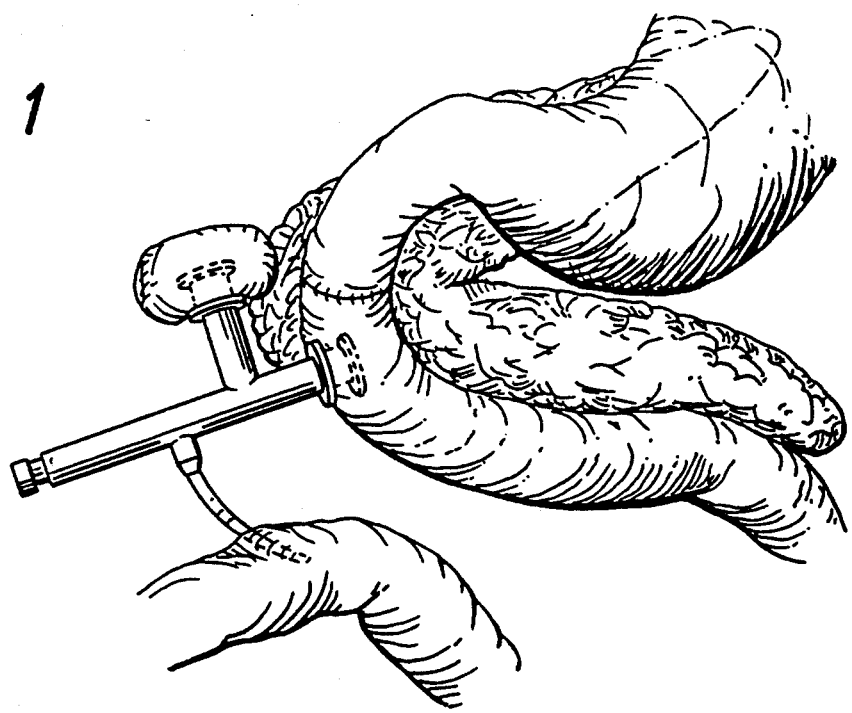
FIG. 1 is a representation of a chronic Herrera pancreatic fistula in a dog as modified for the purposes of the study 1 described below.

The studies on ileal satiety mechanisms were conducted in dogs equipped with chronic Herrera pancreatic fistulas, with a modified design. To create these fistulas, the minor pancreatic duct was ligated; and the portion of the duodenum into which the main pancreatic duct drains was removed from duodenal continuity by transection above and below the duct. This portion of duodenum was then fashioned into a closed, collecting pouch by over-sewing its ends. Duodenal continuity was re-established by suturing the cut ends of the duodenum back together. A stainless steel Herrera cannula which forms a sort of asymmetrical T, was then inserted so that the sidearm drained pancreatic juice from the collecting pouch while one end of the long arm entered the duodenum and the other end exited from the abdomen through a skin incision. When the cutaneous end was kept closed, all pancreatic juice entered the duodenal pouch, flowed thence through the sidearm of the Herrera cannula and into the long arm and from there into the duodenum, so that digestion remained normal. A standard Herrera cannula was used whenever an investigator wished to collect pancreatic juice or to divert pancreatic juice from the duodenum during repeated, acute experiments. This was done by inserting an obdurator, essentially a plug on a long stem that blocks the duodenal end of the long arm of the Herrera cannula while reversing flow of juice out the cutaneous end. The modification (FIG. 1) used in this study involved putting a second sidearm in the form of a nipple on the Herrera cannula. One end of a short piece of Tygon tubing was attached to the nipple, while the other end was tunneled through and secured in the bowel wall at the midpoint of small intestine. (To do this, the surgeon pulled the mobile small intestine toward the Herrera cannula, so that the distance the Tygon tube had to traverse was quite short).

Figure 2:
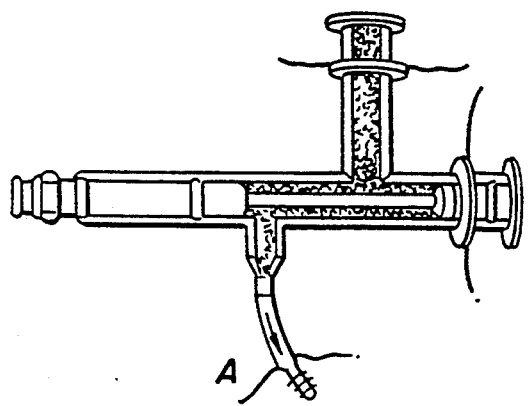
FIG. 2 is an enlarged view of FIG. 1, showing the modified Herrera cannula into which has been inserted an obdurator which directs the flow of pancreatic juice into the ileum.
Figure 3:
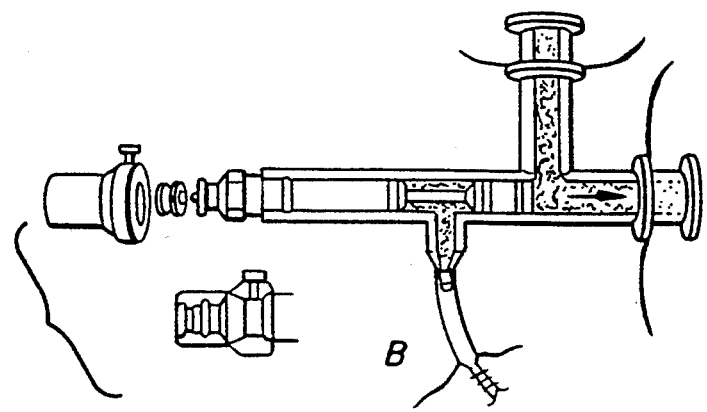
FIG. 3 is an enlarged view of FIG. 1, showing the modified Herrera cannula into which has been inserted an obdurator which directs the flow of pancreatic juice into the duodenum.

As illustrated in FIGS. 2 and 3, detailed drawings of the cannula design, two different obdurators, equipped with double O-rings to provide water tight seals, were used to direct the flow of pancreatic juice, either into the duodenum (FIG. 3), the normal situation, or into the distal half of small intestine (FIG. 2), an abnormal route. The routings could be changed in about 2 minutes by unscrewing the cover cap (FIG. 3), which is outside the abdominal wall, changing the obdurator, and replacing the cover cap. The obdurator in FIG. 3 was also designed so that water could be injected under pressure through the Tygon by-pass conduit to assure its patency through such periodic irrigations. This study was a double crossover design to minimize the effects of weight loss; that is, only eight day periods were used so that any weight loss would be limited to minor amounts. It was an objective of the study to determine how digestion in the proximal bowel (the normal pathway) vs. in the distal bowel, affected food intake. Since weight loss stimulates the brain to override normal satiety mechanisms, profound weight loss could mask real differences in satiety responses between proximal and distal digestive pathways. Thus, the protocol was designed so that after a base line period of normal digestion, the dogs would undergo four successive 8 day periods. The subject dogs were designated either group A dogs or group B dogs. In group A, pancreatic juice was diverted to distal intestine for the first 8 day; it was then returned to duodenum for the second 8 day; for the third 8 day period it was again diverted to distal bowel; and in the final fourth 8 day period, it was again returned to the duodenum. In group B, pancreatic juice entered the duodenum in the first 8 day period, and then in successive 8 day periods, the distal bowel, the duodenum and finally the distal bowel. Wherever the pancreatic juice was going, the dogs had the obdurators changed every 4 days so that (a) the by-pass conduit could be irrigated and (b) the manipulators would be multiplied so that the dogs could less easily understand how they were being manipulated (i.e., they were blinded to their treatments). Whatever the treatment, the dog was allowed to eat freely from a bucket which contained 4000 grams of a standard kibble dog food.

At the same time every morning for each of the 32 days of the study, the bucket was weighed to determine the amount of dog food consumed in the 24 hour period. Also, every second day, each dog was weighed. The dogs were housed in outdoor kennels, so there was no control of environmental temperature. However, studies were conducted throughout the year so that there was no seasonal bias. Eleven dogs were studied, six dogs in group B and five dogs in group A.

Figure 4:
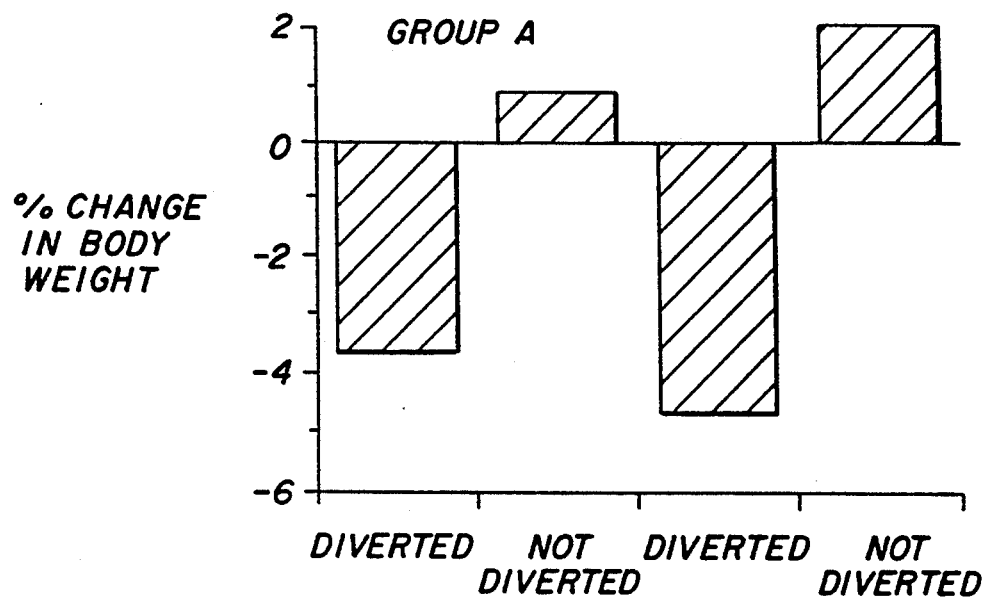
FIG. 4 is a graphic representation of the results of the study 1 described below.
Figure 5:
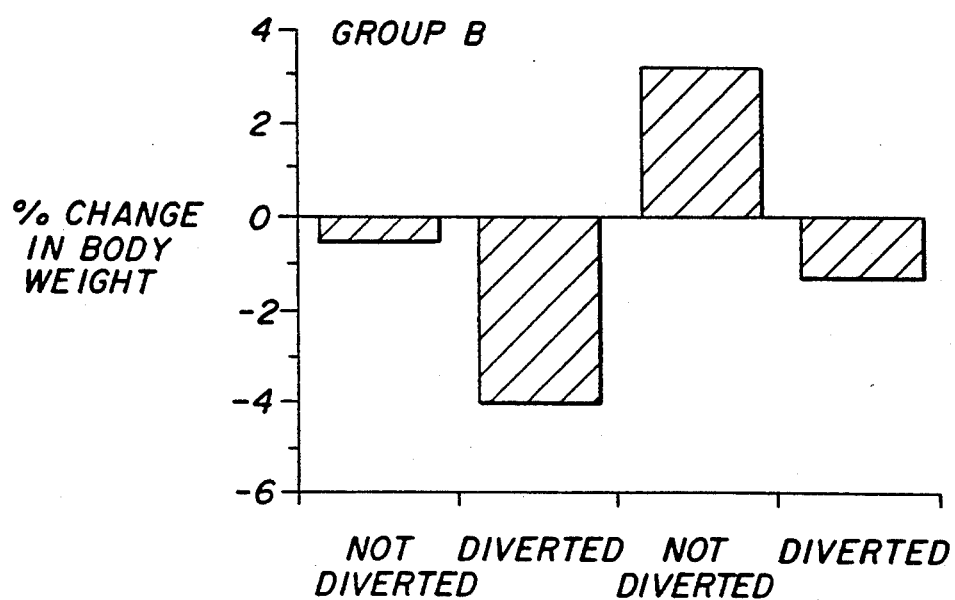
FIG. 5 is a second graphic representation of the results of the study 1 described below.
Figure 6:
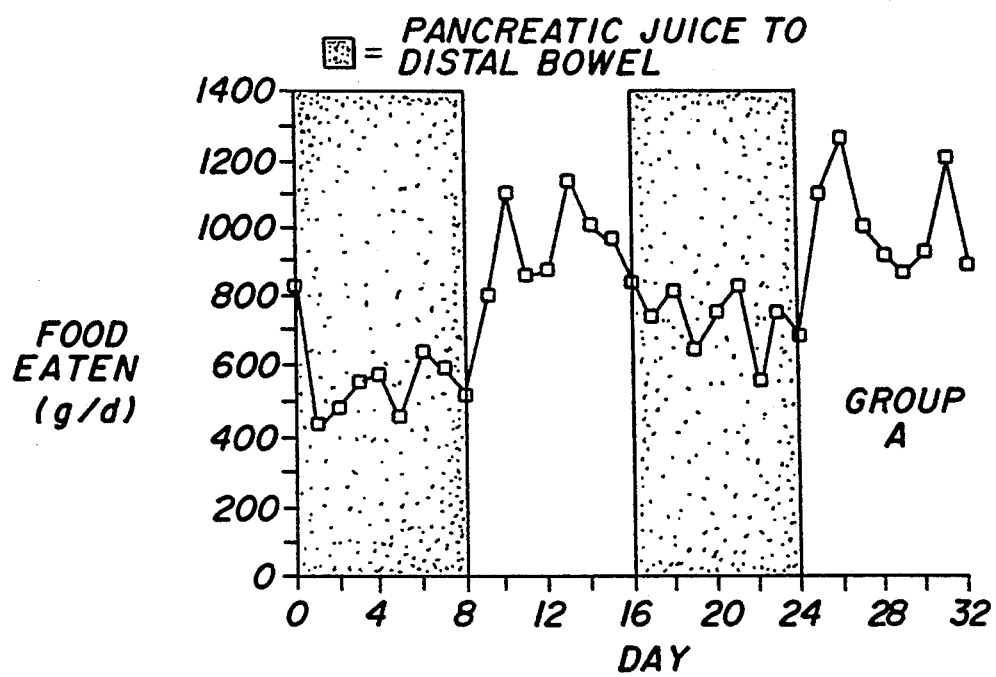
FIG. 6 is a third graphic representation of the results of the study 1 described below.
Figure 7:
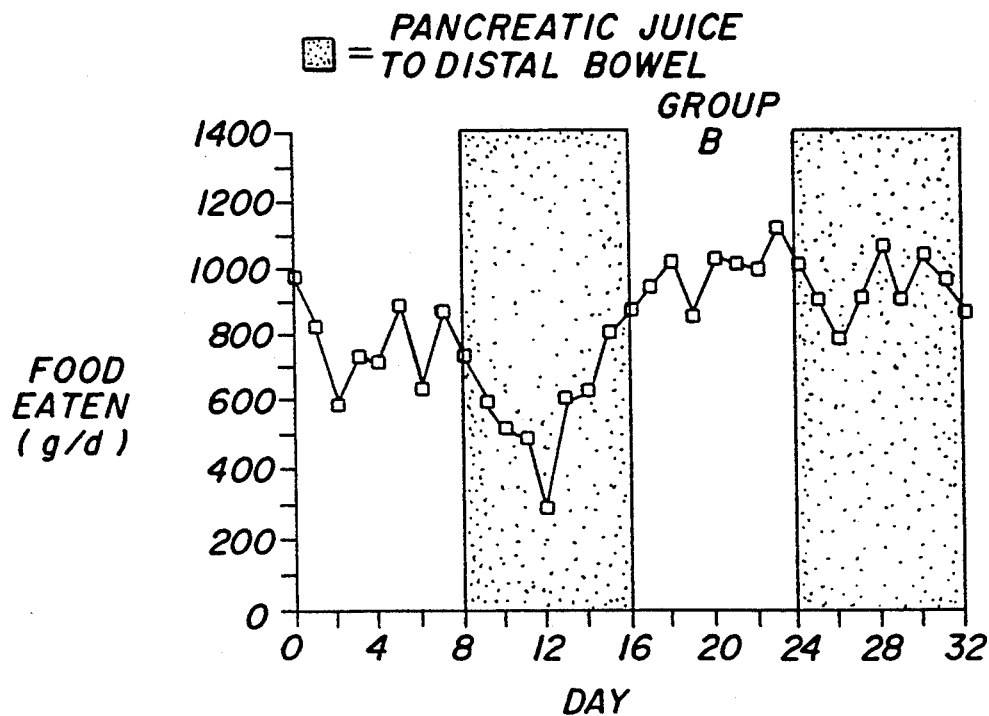
FIG. 7 is a fourth graphic representation of the results of the study 1 described below.

In either group, diverting the pancreatic juice to the distal bowel consistently reduced food intake (FIGS. 6 & 7) and body weight (FIGS. 4 & 5). The magnitude of the reduction in food averaged (between the two periods of diversion within dogs) in individual dogs from −12% (only one dog showed no reduction) to 52%. The "gorgers" (those dogs that tended to wolf down their food quickly in one large daily feed) were less affected by pancreatic juice diversion than the "nibblers" (those dogs that ate small amounts frequently throughout the day). The one dog that did not respond was a pronounced "gorger." Food intake and percent weight change during the two periods of diversion were averaged in each animal and compared by paired T test with the corresponding average in the same animals from the two periods of normal, duodenal entry of pancreatic juice. Food intake was statistically significantly ($p<0.005$) lower and weight loss was statistically significantly ($p<0.0005$) greater in the 11 dogs during the periods of diversion of the pancreatic juice to the distal small intestine.

The patterns that emerged from the double crossover design strongly support the idea that distal routing suppressed appetite. Thus, as impressive as the diminished food intake during the periods of diversion, was the rebound hyperphagia when the juice was routed back to the duodenum in the next 8 day period.

Study 2

Determination of Optimal Nutrient(s). The object of this study is to find the most potent inhibitor at the most sensitive site. 100 rats with chronic cannulation of intestine are chronically fed over several successive days. A selected site along each rat's intestine is surgically linked to an 8 channel, small volume perfusion pump using standard techniques. Single or two-channel tethers are used to allow rat free movement and feeding during the study. The ileum or other selected segment of gut, is perfused with either NaCl as the control or with the nutrient to be tested, before and during daily feeding times. Food consumption during perfusion is measured. Dose-response data is generated, to show relative potencies of glucose, oleate, dodecanoate, phenylalanine, and various polypeptides infused in the ileum and in other parts of the intestine. This assay model may be used to determine whether combinations of nutrients are more potent than single nutrients; and/or whether multiple delivery sites are better than a single region of the bowel. Also, simultaneous infusion through two spaced infusion ports in terminal ileum might may be used to determine whether spaced release, as opposed to single point release, enhances potency. The advantages of this assay are that chronic feeding, testing of agent over several successive days, causes less perturbation than acute, sham-feeding, models; it also allows a determination as to whether the effect wears off with time.

Study 3

Confirmation in Man: The optimal nutrient or nutrient combination determined from example 2 is tested in normal volunteers independently of any dosage form, using chronic intestinal intubation with single or multilumen perfusion tubes properly sited along the bowel. Again, the amount of food consumption during perfusion of nutrient is measured against the amount of food consumption during perfusion of the control. Two 1 mm perfusion lumens are easily tolerated for several days by experienced or naive subjects. A four day test schedule per subject allows adequate comparison of 2 doses of nutrient against control infusions.

Study 4

Preliminary dosage formulation: Glucose in ileum is 4 times more potent at inhibiting gastric emptying of solid food than glucose in jejunum. Therefore, to test an ileal delivery system, doses of glucose are separately coated with a rapidly dissolving coating (one that comes off in the duodenum) and with a delayed release coating (one that comes off in the ileum). Thus, the ileal-releasing preparation should significantly inhibit gastric emptying more than the jejunal-releasing preparation. The subjects are allowed to eat freely, three times a day. After a baseline period of normal consumption, a dosage of glucose is administered with each meal, coated with either the rapidly dissolving or the slowly dissolving coating. Gastric emptying is monitored using standard techniques. The test takes as little as 2 weeks. Once confirmed, the desired satiety agent is similarly tested, replacing the glucose and using similar coatings.

Study 5

The proposed coating(s) are used to encapsulate the non-absorbable marker, polyethylene glycol 14C-PEG. 10% of the coated particles are overcoated with 113 m-in-plexiglass and used to determine, with gamma scintigraphy, the rate of delivery of the drug particles to terminal ileum (previously outlined with 99 m-Tc). Simultaneously, a double-lumen, marker-perfusion system in the ileum is used to determine the extent to which the 14C-PEG has been released from the other 90% of entericly coated particles. This study is carried out in a few weeks and is used repeatedly in different volunteers to test several different delivery vehicles.

Study 6

The product is tested in several ways. Because of CNS compensation, however, weight loss per se is not consistently achieved on a 40% reduction of intake of food alone. In a cross-over trial with limited numbers of normal or obese volunteers, it is tested against a placebo to determine whether it reduces food consumption. The agent is tested against placebo as an adjunct to sustain weight loss in obese subjects who have just completed a weight reduction program. And, it is tested against a placebo for inducing weight loss in obese subjects who are undergoing an exercise program.

DESCRIPTION OF THE PREFERRED EMBODIMENTS

The preferred enteric coating is a pH sensitive polymer that dissolves at the neutral to slightly alkaline pH of the human ileum (pH 7.5). A commonly used currently approved coating of this nature is Eudragit S, Rohm Pharma GmbH, Welsterstadt, Germany.

The use of a pH-sensitive coating has the advantage of targeting coating dissolution to the ileum, independent of transit time. Along the human GI tract, the stomach is very acidic (pH 1.5–4.5) and the proximal bowel is below neutral pH (pH 6.0–6.5); but the pH rises to a peak of 7.8 in the distal small intestine because of the increasing predominance of bicarbonate anion secretion by small intestinal mucosa into the lumen. Eudragit S is a weak acid polymer which is insoluble below pH 7 and thus tends to rupture in the ileum, where the contents of drug formulation would be disgorged. There are other forms of targeting to regions; for example, an enteric coating made of diazotized polymer may be solubilized as anaerobic bacteria in the terminal ileum and cecum, reduce and thus split the diazo bond. Nevertheless, the concentration of such bacteria in more proximal ileum is unknown, so a pH sensitive mechanism is preferred in the current context.

There are also enteric coatings, such as hydroxy cellulose, that rupture with time as they slowly hydrate and swell to bursting. It is common to achieve a 2–3 hour delay to burst with such materials. Nevertheless, it is desirable to have release specifically in the ileumfree to adjust moultaneously free to adjust mouth to ileal transit by altering gastric residence time through particle diameter. Using a time dependent, rather than a site or pH dependent, mechanism impairs this freedom in the design of the dosage form.

Sodium dodecanoate or sodium dodecylsulfate are the preferred active ingredients. Since the availability of pancreatic enzymes to digest polymeric nutrients in the ileum is unpredictable, the nutrient should be in a predigested (monomeric) form. While it is known that glucose is very active in canine ileum at slowing gastric emptying and most likely is similarly active in the human ileum, acute experiments indicate that glucose is not a good satiety agent in the ileum, but that fat is. Furthermore, fatty acids, like dodecanoic acid, are much more slowly absorbed than glucose, so that even small amounts may achieve a long length of contact.

Since the preferred enteric coating is pH sensitive, its contents should re-enforce the pH of the lumen, rather than promote a different pH. For example, if small amounts of water leak through cracks into the coated sphere and hydrate the content, and alkaline pH on the interior surface of the coating may speed coating dissolution with premature rupture despite an acidic, luminal pH around the outside of the coating. Sodium dodecanoate, on dissolution in water, achieves a pH of about 8.0, whereas bicarbonate-rich ileal juice is at a pH of around 7.5. By contrast, sodium oleate achieves a pH around 9.5 and so may promote premature rupture of the coating even in the jejunum. Nevertheless, even sodium dodecanoate is a weak acid buffer and therefore may speed coating dissolution.

The other preferred active ingredient is sodium dodecylsulfate. This material is known to be biologically active—for example, when in the proximal intestinal lumen, it stimulates pancreatic secretion even better than dodecanoic acid—but since it is a stronger sulfonic, rather than a weaker carboxylic acid, it does not have the buffering effect that could lead to premature rupture of a pH sensitive coating. On the other hand, dodecanoate is a natural foodstuff, whereas dodecylsulfate is not, so that the commercial choice might be potentially influenced by FDA requirements for toxicity studies.

Sodium dodecanoate and sodium dodecylsulfate are much more readily soluble at luminal pH than sodium oleate. The dodecanoate does not require bile salt to emulsify it, whereas dispersion of sodium oleate would be aided by bile salt. Dispersion into solution is necessary for the nutrient to contact the sensory nerves in the intestinal mucosa.

The density of enteric-coated particles comprising the dosage form may be about 1.0 and the diameter about 2.0 mm. These may be ingested at mealtime as a slurry in a pleasant tasting but low calorie drink. The drink may have a pH of less than 6 and may be, for example, orange juice or coffee. The slurry and the drink may also be marketed together. The size and density are designed to place the dosage form in the ileum for maximum efficacy at the time of the next meal, 4–6 hours later. The slurry provides unconstrained ability to adjust the active dose.

Fatty acids have densities around 0.80 and sodium salts of fatty acids about 0.90. Enteric-coated particles made up of these substances, however, have a density close to 1.0 because of the weight of the enteric coating. It is known that particles less or more dense than 1.0 empty from the stomach more slowly than particles of the same diameter but a density of 1.0. Since the knowledge of human gastric emptying of spheres of different sizes is derived almost entirely from study of spheres with a density of 1.0, a particle with a density of 1.0 is desirable in order to predict its behavior. If the coated particles of sodium dodecanoate are significantly less dense than 1.0, the density of the particles may be increased by including an incipient, such as NaCl of trisodium citrate. Trisodium citrate buffers to pH 5 and thus may counteract the more alkaline buffering of the sodium dodecanoate.

A particle with a density of 1.0 and a diameter of 2.0 mm may have a gastric residence such that about half of the particles would empty from the stomach in 150 minutes after ingestion. It is known that postcibal transit from human pylorus to cecum averages 100-150 minutes. Thus median transit from mouth to mid ileum would be 200-250 minutes with this dosage form. This transit may place the bulk of the dosage in the ileum by the time of the next meal, 4-6 hours later. Since postcibal pylorus to cecum (i.e., small intestinal) transit time seems to be constant regardless of particle size, whereas the gastric residence can be shortened or lengthened by changing particle diameter, the time of arrival of the drug particles into ileum may be modified, as needed, by adjusting the size of the particles in the formulation.

It is now known from canine and human studies that while the half-time of gastric emptying of small particles is determined by particle diam and density, the number of particles emptied per time varies directly with the number ingested, independent of meal size (i.e., of the amount of solid food ingested). Thus, the absolute amount of active ingredient arriving in the ileum 4-6 hours after ingestion may be regulated independently from the transit time of the particles by regulating the number of particles ingested in the slurry. Furthermore, the number of particles needed depends, as well, on the ratio of volumes of active ingredient to coating. The optimum dosage, therefore, can be achieved by adjusting the concentration (i.e., number of teaspoons of particles per glass of drink) or total amount of particles in the slurry.

The appetite control composition of the invention may be used as an adjunct to a weight loss program to reduce increased hunger or craving for food during the forced restriction in caloric intake. Alternatively, the composition of the invention may be used as a direct weight-loss-maintenance device, effective by virtue of the ability of the composition to reduce food intake by about 40%; or, the composition of the invention may be used as an adjunct to a restricted weight-loss-maintenance diet, effective by virtue of the ability of the composition to induce satiety.

The invention disclosed herein is not considered to be limited to the preferred embodiments. It is contemplated that any method for the control of appetite which includes selective delivery to the ileum of food grade nutrients, is within the scope of the invention.

I claim:

1. A method for controlling appetite comprising:
   selecting a pharmaceutically acceptable satiety agent;
   selecting a pharmaceutically acceptable delivery agent which will release the satiety agent predominantly in the ileum;
   formulating a dosage form;
   and orally administering to a subject a dosage effective to produce a satiety sensation at a meal time subsequent to the administration of the dosage.

2. A method according to claim 1 further comprising:
   administering said satiety agent to the subject at such a time that maximum satiety occurs at about the next meal time.

3. A method according to claim 1 wherein the dosage is in a multi-particle capsule form.

4. A method according to claim 1 wherein the satiety agent comprises an active ingredient selected from the group consisting of sugars, free fatty acids, polypeptides, amino acids, structural analogs thereof, and mixtures thereof, and wherein the pharmaceutically acceptable delivery agent is selected from the group consisting of enteric coatings.

5. A method according to claim 4 wherein the enteric coating is selected from the group consisting of pH sensitive polymers, diazotized polymers, and cellulosic polymers.

6. A method according to claim 5 further comprising encapsulating the selected active ingredient with the selected enteric coating into particles of between 1 and 3 millimeters in diameter.

7. A method according to claim 6 wherein the particles have a density of between 0.5 and 2.0.

8. A method according to claim 7 wherein the particles have a density of between 0.75 and 1.25.

9. A method according to claim 8 further comprising administering the particles in a multi-particle capsule form.

10. A method according to claim 8 further comprising mixing the particles with a liquid, and administering the resultant mixture to an animal.

* * * * *